United States Patent [19]

Johnson et al.

[11] 4,125,396
[45] Nov. 14, 1978

[54] COMPOSITION AND METHOD FOR DEFOLIATION

[75] Inventors: Bruce N. Johnson; Louis P. Cartsunis, both of Oklahoma City, Okla.

[73] Assignee: Kerr-McGee Chemical Corporation, Oklahoma City, Okla.

[21] Appl. No.: 882,316

[22] Filed: Mar. 1, 1978

Related U.S. Application Data

[63] Continuation-in-part of Ser. No. 786,142, Apr. 11, 1977, abandoned.

[51] Int. Cl.$^2$ .................. A01N 9/02; A01N 13/00
[52] U.S. Cl. ................................. 71/70; 71/69; 71/DIG. 1
[58] Field of Search ............... 71/69, 70, DIG. 1

[56] References Cited

U.S. PATENT DOCUMENTS

| 1,534,289 | 4/1925 | Teppet et al. | 71/128 |
|---|---|---|---|
| 1,914,969 | 6/1933 | Chipman | 71/128 |
| 2,704,243 | 3/1955 | Seibert | 71/69 |
| 2,749,227 | 6/1956 | Bales | 71/69 |
| 3,433,622 | 3/1969 | Plonsker et al. | 71/70 |
| 3,442,638 | 5/1969 | Wollensak et al. | 71/70 X |
| 3,480,658 | 11/1969 | Robs | 71/70 X |
| 3,867,125 | 2/1975 | Jenney et al. | 71/69 |

OTHER PUBLICATIONS

McCutcheon's, Detergents & Emulsifiers, 1972 annual, pp. 20, 99, 166.
McCutcheon's, Detergents & Emulsifiers, North American Ed., 1973 annual, pp. 97, 186.

*Primary Examiner*—Joseph Paul Brust
*Attorney, Agent, or Firm*—William G. Addison

[57] ABSTRACT

This invention relates to an improved composition of matter for and method of defoliating plants such as, for example, cotton. More particularly, this invention relates to an improved fire retardant defoliant comprising an aqueous solution of an alkali metal chlorate, alkali metal carbonate, urea and a surfactant comprising a mixture of alkali metal alkenesulfonates and alkali metal hydroxyalkanesulfonates and a method for using the same.

9 Claims, No Drawings

COMPOSITION AND METHOD FOR DEFOLIATION

PRIORITY DATA

This application is a continuation-in-part of application Ser. No. 786,142, filed Apr. 11, 1977, now abandoned.

BACKGROUND OF THE INVENTION

1. Field of the Invention

This invention relates to compositions of matter for and methods of defoliating plants. More specifically, through not be way of limitation, this invention relates to the defoliation of plants such as, for example, cotton.

2. Description of the Prior Art

It has been known for some time that an aqueous solution of an alkali metal chlorate is an effective defoliant. Sodium chlorate is low in cost and readily available, therefore, it generally is preferred. Further, it is known that the defoliant may contain additional additives such as surfactants, fire retardants, corrosion inhibitors and the like, but little if any research in this regard has been conducted in the past.

Defoliation of plants at certain stages in their growth has many advantages. For example, in the case of cotton plants, defoliation enhances the drying of the cotton bolls and improves or at least maintains the quality of the cotton through a reduction of boll rot and a decrease in the straining of the cotton as it is mechanically harvested.

Numerous other types of plant life frequently are defoliated to facilitate harvest such as, for example, rice, sunflower, soybean plants and the like.

Sodium chlorate, however, is a strong oxidizer and greatly accelerates the burning rate of flammable matter. It is for this reason that sodium chlorate should not be used alone as a defoliant because the fire hazard it creates is too great to be tolerated. It has been known, heretofore, to use sodium carbonate as a fire retardant additive to solutions of sodium chlorate. An example of such a combination is disclosed in U.S. Pat. No. 1,534,289.

U.S. Pat. No. 2,704,243 discloses various boron containing compounds for use as fire retardant additives to chlorate solutions. Examples of such boron containing compounds include sodium metaborate, sodium pentaborate and certain other polyborates. However, such boron containing compounds are expensive, thus, their inclusion within the defoliant necessarily increases the cost of the defoliant. Further, boron compounds, even in low concentration, frequently are toxic to plant life and therefore are undesirable in areas that have soils containing naturally occurring high boron concentrations.

In U.S. Pat. No. 1,914,969 it is suggested that certain alkaline earth metal chlorides such as, for example, calcium chloride, are effective fire retardant additives for sodium chlorate solutions. Obviously, of course, continued use of such additives will necessarily result in contamination of the soil with chlorides from the materials which are also undesirable in some areas.

In U.S. Pat. No. 2,749,227 it is suggested that the addition of sodium metaborate to sodium chlorate enhances the defoliant action of the sodium chlorate.

More recently in U.S. Pat. No. 3,867,125, assigned to the same assignee as the present inventor, it is suggested that a combination of an alkali metal carbonate and urea impart greater fire retardancy to a sodium chlorate solution than do either alone and that additional additives such as surfactants may be present. However, this patent fails to provide any indication as to preferable surfactants for addition to sodium chlorate-containing defoliants nor any indication as to the subsequent effectiveness of such a defoliant to which a surfactant has been added.

SUMMARY OF THE INVENTION

An improved fire retardant chlorate based defoliant containing a surfactant and method of using the same has now been discovered. Broadly, the present invention comprises the discovery that a defoliant comprising an aqueous solution of an alkali metal chlorate, alkali metal carbonate, urea and a surfactant comprising a mixture of alkali metal alkenesulfonates and alkali metal hydroxyalkanesulfonates exhibits superior defoliation in comparison to other defoliants and other surfactants. Further, the defoliant hereinafter described contains little, if any, of the potentially undesirable borates or chlorides of the previously described defoliants.

The combination of alkali metal carbonate and urea are present in an amount sufficient to provide a ratio of such combination to chlorate within the range of from about 0.2:1 to 1.2:1 and a ratio of carbonate to urea within the range of from about 1:4 to 4:1. The alkali metal chlorate is present in an amount of from about 1 to 30 percent by weight solution basis. The surfactant comprising a mixture of alkali metal alkenesulfonates and alkali metal hydroxyalkanesulfonates is present in an amount of from about 0.5 to 6.0 percent by weight solids basis.

DESCRIPTION OF THE PREFERRED EMBODIMENTS

The alkali metal chlorates contemplated herein include sodium, potassium and lithium chlorate. For economic reasons, sodium chlorate is the preferred alkali metal chlorate.

The alkali metal chlorate may be present in an aqueous solution of the defoliant in an amount of from about 1 percent to as high as 30 percent by weight. As those versed in the art will appreciate, in addition to the dry form, the chlorate solution generally is shipped in a concentrated form for convenience and to reduce handling cost, thus, the solutions generally are sold and transported in concentrations of from about 5 to 30 percent by weight sodium chlorate. The chlorate solution is applied, however, in substantially lower concentrations. Indeed, sodium chlorate has been found to be effective when applied in concentrations as low as 0.5 percent. Generally, however, the chlorate is applied in concentrations of from about 1 to about 8 percent by weight. A particularly preferred concentration for application to plants is in the range of from about 1 to about 4 percent by weight.

It is known that when urea and an alkali metal carbonate are added to chlorate solutions in certain specific ratios, they act synergistically providing an improved fire retardant defoliant. The alkali metal carbonates contemplated herein include sodium, potassium and lithium carbonate. The preferred carbonate is sodium carbonate.

It is essential that the combination of alkali metal carbonate and urea be present in an amount sufficient to provide a ratio of such combination to chlorate within the range of from about 0.2:1 to 1.2:1 and a ratio of carbonate to urea within the range of from about 1:4 to 4:1.

It is preferred that the sodium carbonate and urea be present in an amount sufficient to provide a ratio of carbonate and urea to chlorate within the range of from about 0.5:1 to 1:1 and particularly good results have been obtained at a ratio of about 0.75:1. It is also preferred that the ratio of sodium carbonate to urea be within the range of from about 1:3 to 3:1 and particularly good results are obtained at ratios of from about 1:2 to 2:1.

It has been discovered that when a surfactant comprising a mixture of alkali metal alkenesulfonates and alkali metal hydroxyalkanesulfonates is added to the aqueous solution of ingredients hereinbefore described, an improved defoliant is obtained which provides superior defoliation in comparison to other defoliants and other surfactants.

It is essential that the mixture of alkali metal alkenesulfonates and alkali metal hydroxyalkanesulfonates be present in an amount of from about 0.5 to 6.0 percent by weight of solid to obtain the resultant superior defoliation. Obviously, of course, greater amounts of surfactant can be utilized, however, such addition may be uneconomical. It is preferred that the mixture of alkali metal alkenesulfonates and alkali metal hydroxyalkanesulfonates be present in an amount of from about 0.75 to 2.0 percent by weight of the dry defoliant compound.

The sulfonates as contemplated in this invention are the alkali metal salts resulting from neutralization of the reaction products of alpha olefins and sulfur trioxide produced, for example, in continuous, thin film, sulfonation reactors.

The alpha olefins contemplated herein are of the generalized formula:

$$R - CH = CH_2$$

wherein R represents radicals having the generalize formula:
$$C_nH_{2n+1}$$

and wherein $n$ is an integer of from about 10 to about 18. Preferably, $n$ is an integer of from about 12 to about 14.

Sulfonation of the alpha olefins produces a mixture of reaction products. Two reaction paths account for the formation of the major products. One path, direct insertion of $SO_3$, results in the formation of alkenesulfonicacids with concomitant migration of the double bond as illustrated by the generalized equation for the reaction:

$$R - CH = CH_2 + SO_3 \rightarrow R' - CH = CH - (CH_2)_x SO_3H$$

wherein R' represents radicals having the generalized formula:

$$C_{n'}H_{2n'+1}$$

Wherein the value of $n'$ is such that $n' + x$ equals the integer $n$ of the corresponding alpha olefin.

The second path results in the formation of sultones. Those which have been identified are of the generalized formulas:

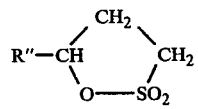

and

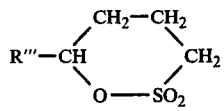

and under some circumstances the formation of small amounts of four-membered ring sultones can occur. The radicals R", R''' and the like are of the general chemical formula: $C_{n''}H_{2n''+1}$, $C_{n'''}H_{2n'''+1}$ and the like, the subscripts $n'$, $n'''$ and the like denoting integers such that the total number of carbon atoms in the sultones is the same as the corresponding alpha olefin from which it was formed. It is to be understood that other sultones, as yet unidentified, also may be present. Further, small amounts of disulfonicacids or sultonesulfonicacids of various configurations may be present.

Hydrolysis of the mixture of alkenesulfonicacids and sultones with aqueous alkali metal hydroxides of the generalized formula MOH, wherein M represents the alkali metal, yields a mixture of the corresponding alkali metal alkenesulfonates having the generalized formula:

$$R' - CH = CH - (CH_2)_x SO_2O^-M^+;$$

and alkali metal hydroxyalkanesulfonates having the identified generalized formulas:

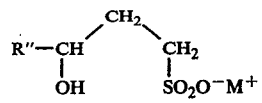

and

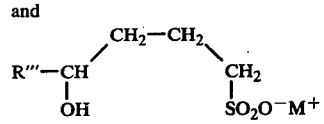

Further, small amounts of alkali metal disulfonates of various configurations may be present in the mixture. The alkali metal hydroxides contemplated herein include sodium, potassium and lithium hydroxide. The preferred alkali metal hydroxide is sodium hydroxide.

Typically, the surfactant will consist of from about 45 percent to about 65 percent of the alkali metal alkenesulfonate and from about 30 percent to about 45 percent of the alkali metal hydroxyalkanesulfonate, the remainder comprising disulfonates of various configurations.

An example of a preferred defoliant composition for direct application to plants comprises an aqueous solution containing from 1 to about 4 percent by weight sodium chlorate in admixture with sufficient sodium carbonate, urea and a surfactant comprising a mixture of sodium alkenesulfonates and alkali metal hydroxyalkanesulfonates to provide a ratio of said carbonate and urea to chlorate within the range of from about 0.75:1 to 1:1 and a ratio of carbonate to urea within the range of from about 1:3 to 3:1 and sufficient surfactant to be present in an amount of from about 0.75 to 2.0 percent by weight of the dry defoliant compound.

The concentrated defoliant usually is diluted with water prior to its application to plants. When the concentrated defoliant is diluted for application to plants, it generally contains from about 1 to 8 percent by weight sodium chlorate, and generally is applied in amounts of from about 4 to about 10 gallons per acre by aerial spray or in amounts of from about 15 to about 30 gallons per acre by ground spray. As those versed in the art will appreciate the exact formulation and amount applied will vary depending upon the area, type of plant to be defoliated and the like.

EXAMPLE 1

To determine the effectiveness of various surfactants in combination with defoliants, field trials were conducted at and with the cooperation of the USDA Agriculture Research Station at Weslaco, Texas. The following criteria governed the selection of surfactants for evaluation:

1. An increase in the performance of the aqueous solution of alkali metal chlorate disclosed herein as a defoliant over and above the performance obtained with other defoliants plus a surfactant;
2. Compatibility with sodium chlorate;
3. Preferably a dry material to be compatible with the other dry ingredients;
4. Preferably a non-ionic or anionic compound for compatibility with hard waters (high mineral content water); and
5. Economic availability.

As a result, the surfactants given in Table I were selected to be tested with the aqueous solution hereinbefore described, a sodium chlorate-urea defoliant and Def-6 a tributyl phosphorotrithioate produced by Chemagro Company. The surfactants and their combination with the defoliants used in this trial are given in Table II.

TABLE I

Surfactants Selected for Evaluation

Witco-Sulframin-14/16 AOS (mixture of sodium salts of alkenesulfonates and hydroxyalkanesulfonates)
Lakeway-301-10 (F&P) (mixture of sodium salts of alkenesulfonates and hydroxyalkanesulfonates)
Bio-Terge AS-90F (mixture of sodium salts of alkenesulfonates and hydroxyalkanesulfonates)
Petro-AGS (sodium mono and di-methylnapthalene sulfonate)
Petro-Morwet B (sodium butyl napthalene sulfonate)
Petro-Morwet M (sodium mono and dimethyl napthalene sulfonate)
Atplus 522 (Anionic surfactant with coupling agents)
Atplus 526 (nonionic surfactant with sticking agents)
Renex 35 (Polyoxyethylene (12) tridecyl ether urea complex)
Triton X-100 (alkyl aryl polyoxyethylene glycol)
Nalcatrol (polyvinyl polymer)

| | | Defoliant/Surfactant Combinations and Ratios | | |
|---|---|---|---|---|
| Test | Defoliant | Normal Appln. Rate Lb/Acre or Pint/Acre | Surfactant | Surfactant % by Wt., Dry Solids Basis |
| 1 | Sodium chlorate - urea | 3.0/1.5 | none | — |
| 2 | Sodium chlorate - urea | 3.0/1.5 | Nalcatrol | 0.10 |
| 3 | Sodium chlorate - urea | 3.0/1.5 | Sulframin 14/16 AOS | 1.40 |
| 4 | Def-6 | 4 pts. | Nalcatrol | 0.10 |
| 5 | Def-6 | 4 pts. | Sulframin 14/16 AOS | 1.40 |
| 6 | alkali metal chlorate-alkali metal carbonate - urea* | 6.0 | None | — |
| 7 | " | 6.0 | Sulframin 14/16 AOS | 0.70 |
| 8 | " | 6.0 | Sulframin 14/16 AOS | 1.40 |
| 9 | " | 6.0 | Sulframin 14/16 AOS | 2.80 |
| 10 | " | 6.0 | Sulframin 14/16 AOS | 5.60 |
| 11 | " | 6.0 | Sulframin 14/16 AOS, Nalcatrol | 1.40, 0.10 |
| 12 | " | 6.0 | Sulframin 14/16 AOS, Nalcatrol | 2.80, 0.10 |
| 13 | " | 6.0 | Petro-AGS | 1.40 |
| 14 | " | 6.0 | Lakeway 301-10 (F & P) | 1.40 |
| 15 | " | 6.0 | Bio-Terg AS-90F | 1.40 |
| 16 | " | 6.0 | Morwet B | 1.40 |
| 17 | " | 6.0 | Morwet M | 1.40 |
| 18 | " | 6.0 | Atplus 522 | 3.00 |
| 19 | " | 6.0 | Atplus 526 | 3.00 |
| 20 | " | 6.0 | Triton X-100 | 1.40 |

*the defoliant of this invention, hereinbefore described

The tests were conducted on plots of 200 square feet delineated within a 10 acre field at the research station at Weslaco, Texas. The plots comprised three rows of double-row cotton on 40-inch centers, and were 20 feet long. Each plot was staked and numbered randomly with two replicates to which a 3X normal defoliant application was applied and four replicates to which a normal defoliant application was applied.

The cotton was Tamcot SP 37, a short season cotton with a 30-day bloom period, exhibiting very rapid fruiting and low fertility and pesticide requirements. The average staple length was about one inch. The cotton ranged from about 2.5 to about 4 feet in height and had a boll set two-thirds of the height of the plant with all bolls about one inch in diameter. Two applications of Guthion insecticide had been made. There was no fertilization.

At the time of testing, the cotton plots were mature and ready for harvest; however, regrowth had been stimulated by substantial rain which fell just prior to the application of the defoliants. Moisture was so abundant that the cotton seeds in the bolls on the lower portion of the plants started to sprout and mold; both terminal and basal regrowth developed and was extremely difficult to control.

Because of the wet weather and resulting regrowth, two separate application rates of defoliant were used; one a typically normal rate and the other three times the normal rate. The above-normal rate was used to rapidly show the effects of the various defoliant formulations.

Application of the spray solutions was made with a portable hand boom spray unit. The unit was designed to be easily handled to deliver a uniform spray pattern similar to an aerial application.

The unit had three nozzles located on the boom spaced 15 inches apart, one fixed nozzle located in the center and two swivel nozzles at each end. The spray boom was connected to a pressurized system similar to typical paint spray units. The three nozzles (TeeJet Tip No. 80015), delivered 23 gallons of solution per acre at 20 psi and 4 MPH ground speed. The volume actually applied was 400 ml per 200 feet² plot or 23.03 gallons per acre.

The pressure unit consisted of a 2 quart pressure vessel fitted with a 25 foot, ¼-inch pressure hose for pressure application, and a 6 foot ¼-inch hose for solution transfer to the spray boom. An on-off trigger valve was used for control of solution application. A five pound carbon dioxide compressed gas cylinder fitted with a two stage pressure regulator supplied the desired pressure to the system. This spray unit supplied the required mobility for plot application.

The spray pattern was adjusted to overlap the plant rows so that two series of double rows could be sprayed by walking down one row and spraying on the right, then backing up while spraying on the left.

Defoliation performance was established by determining (1) the percent of actual defoliation by counting leaves of a typical cotton plant in each test plot before and after application of defoliant at timely intervals, (2) the percent effectiveness by visually noting the degree of brown foliage as compared to a loss of foliage and (3) the percent performance by visually noting the degree of overall leaf drop together with the degree of remaining basal and terminal regrowth as overall effectiveness. A perfect defoliant should injure each leaf just enough to cause the formation of the abscission layer on each leaf thus causing it to fall. Injury more severe than this would result in dessicated leaves which stick to the plant and result in more pin trash that must be removed from the cotton.

Defoliation performance as used herein is defined to be the average of percent of leaf drop obtained from leaf counts and percent overall effectiveness visually obtained at four and six days after defoliant application. The results of this determination are given in Table III, below, for the 3X normal applications.

TABLE III

| Defoliation Performance for 3 × Normal Defoliant Applications | |
|---|---|
| Test | % Performance |
| 1 | 73 |
| 2 | 41 |
| 3 | 81 |
| 4 | 64 |
| 5 | 58 |
| 6 | 64 |
| 7 | 81 |
| 8 | 91 |
| 9 | 79 |
| 10 | 83 |
| 11 | 80 |
| 12 | 74 |
| 13 | 80 |
| 14 | 89 |
| 15 | 77 |
| 16 | 74 |
| 17 | 77 |
| 18 | 81 |
| 19 | 75 |
| 20 | 76 |

Analysis of this data resulted in a selective reduction in the number of defoliant solutions tested under normal defoliant application rates. The results of the normal defoliant application rate tests are given in Table IV below.

TABLE IV

| Defoliation Performance for Normal Defoliant Applications | |
|---|---|
| Test* | % Performance |
| 6 | 79 |
| 7 | 83 |
| 8 | 94 |
| 9 | 77 |
| 10 | 89 |
| 13 | 87 |
| 14 | 77 |
| 16 | 90 |
| 17 | 90 |
| 18 | 86 |
| 19 | 85 |
| 20 | 76 |

*samples 1–5, 11, 12 and 15 were deleted based on an analysis of the data presented in TABLE III Clearly, the above results demonstrate the enhanced defoliation obtained through the use of the combination of alkali metal chlorate, alkali metal carbonate, urea, and surfactant comprising a mixture of alkali metal alkenesulfonates and hydroxyalkanesulfonates as described in this invention.

What is claimed is:

1. A defoliant comprising an aqueous solution containing:
   an alkali metal chlorate in an amount of from about 1 to about 30 percent by weight;
   an alkali metal carbonate and urea, said carbonate and urea being present in an amount sufficient to provide a ratio of carbonate and urea to chlorate within the range of from about 0.2:1 to 1.2:1 and a ratio of carbonate to urea within the range of from about 1:4 to 4:1; and
   a surfactant consisting essentially of the reaction products resulting from (i) sulfonation of alpha olefins having the generalized formula:

$$R - CH = CH_2$$

wherein R represents radicals having the generalized formula:

$$C_nH_{2n+1}$$

wherein $n$ is an integer of from about 10 to about 18 and (ii) hydrolysis of the sulfonation products with an aqueous alkali metal hydroxide to yield a mixture of alkali metal alkenesulfonates and alkali metal hydroxyalkanesulfonates, said surfactant present in an amount of from about 0.5 percent to about 6.0 percent by weight.

2. The defoliant of claim 1 wherein the surfactant is present in an amount of from about 0.75 to about 2.0 percent by weight, solids basis.

3. The defoliant of claim 1 wherein $n$ preferably is an integer of from about 12 to about 14.

4. The defoliant of claim 1 wherein the alkali metal sulfonates are formed by hydrolysis with an alkali metal hydroxide selected from the group of sodium hydroxide potassium hydroxide and lithium hydroxide.

5. A defoliant comprising an aqueous solution containing:
   sodium chlorate in an amount of from about 1 to about 30 percent by weight;
   sodium carbonate and urea, said carbonate and urea being present in an amount sufficient to provide a ratio of carbonate and urea to chlorate within the range of from about 0.2:1 to 1.2:1 and a ratio of carbonate to urea within the range of from about 1:4 to 4:1; and a surfactant consisting essentially of the reaction products resulting from (i) sulfonation and alpha olefins having the generalized formula:

$$R - CH = CH_2$$

where R represents radicals having the generalized formula:

$$C_nH_{2n+1}$$

wherein $n$ is an integer of from about 10 to about 17 and (ii) hydrolysis of the sulfonation products with an aqueous alkali metal hydroxide to yield a mixture of alkali metal alkenesulfonates and alkali metal hydroxyalkanesulfonates, said surfactant present in an amount of from about 0.5 percent to about 6.0 percent by weight.

6. The defoliant of claim 3 wherein the surfactant is present in an amount of from about 0.75 to about 2.0 percent by weight, solids basis.

7. The defoliant of claim 5 wherein $n$ preferably is an integer of from about 12 to about 14.

8. The defoliant of claim 5 wherein the alkali metal sulfonates are formed by hydrolysis with an alkali metal hydroxide selected from the group of sodium hydroxide, potassium hydroxide and lithium hydroxide.

9. The defoliant of claim 5 wherein the alkali metal sulfonates comprise a mixture of sodium alkenesulfonate and sodium hydroxyalkanesulfonate.

* * * * *